US006894038B2

(12) United States Patent
Elger et al.

(10) Patent No.: US 6,894,038 B2
(45) Date of Patent: May 17, 2005

(54) USE OF BIOGENIC ESTRIOL DIESTER PRODRUGS FOR THE TREATMENT OF AUTOIMMUNE DISEASES

(75) Inventors: Walter Elger, Berlin (DE); Sybille Beier, Berlin (DE); Harald Von Keyserlingk, Berlin (DE); Frank Dahlke, Berlin (DE)

(73) Assignee: Schering Aktiengesellschaft, Berlin (DE)

( * ) Notice: Subject to any disclaimer, the term of this patent is extended or adjusted under 35 U.S.C. 154(b) by 22 days.

(21) Appl. No.: 10/374,708

(22) Filed: Feb. 27, 2003

(65) Prior Publication Data

US 2004/0077614 A1 Apr. 22, 2004

Related U.S. Application Data

(60) Provisional application No. 60/359,726, filed on Feb. 27, 2002.

(30) Foreign Application Priority Data

Apr. 30, 2002 (EP) .............................................. 02090160

(51) Int. Cl.$^7$ .............................. A61K 31/56; C07J 1/00
(52) U.S. Cl. ....................................... 514/182; 552/617
(58) Field of Search .......................... 514/182; 552/617, 552/505

(56) References Cited

U.S. PATENT DOCUMENTS 4,681,875 A    7/1987  Laurent et al.

FOREIGN PATENT DOCUMENTS

WO       WO 0185154       11/2001

OTHER PUBLICATIONS

Kim Sookhyun et al.: "Mechanisms in the shift toward TH2 during pregnancy: A role for estriol. Treatment of TH1 mediated disease." FASEB Journal, vol. 12, No. 4 Mar. 17, 1998 p. A616 XP001108910.

Kim S et al: "Estriol Ameliorates Autoimmune Demyelinating Disease Implications for Multiple Sclerosis" Neurology, Lippincott Williams & Wilkins, Philadelphia, US, vol. 52, No. 1, Apr. 12, 1999 pp. 1230–1238, XP001026663.

Zang Ying C Q et al.: "Regulatory effects of estriol on T cell migration and cytokine profile: Inhibition of transcription factor NF–kappaB." Journal of Neuroimmunology, vol. 124, No. 1–2, Mar. 2002 pp. 106–114, XP002213672.

Heithecker, R. et al.: "Plasma estriol levels after intramuscular injection of estriol and two of its esters" Horm. Res. (1992), 35(6), 234–8, XP008008290.

*Primary Examiner*—Cecilia J. Tsang
*Assistant Examiner*—Taylor Victor Oh
(74) *Attorney, Agent, or Firm*—Wendy L. Washtien; Ronald S. Hermenau

(57) ABSTRACT

The invention relates to the use of esters of estriol, for example, an estriol 3,17-dipropionate or an estriol 3,17-dihexanoate, for the treatment of autoimmune diseases, such as multiple sclerosis (MS).

15 Claims, 1 Drawing Sheet

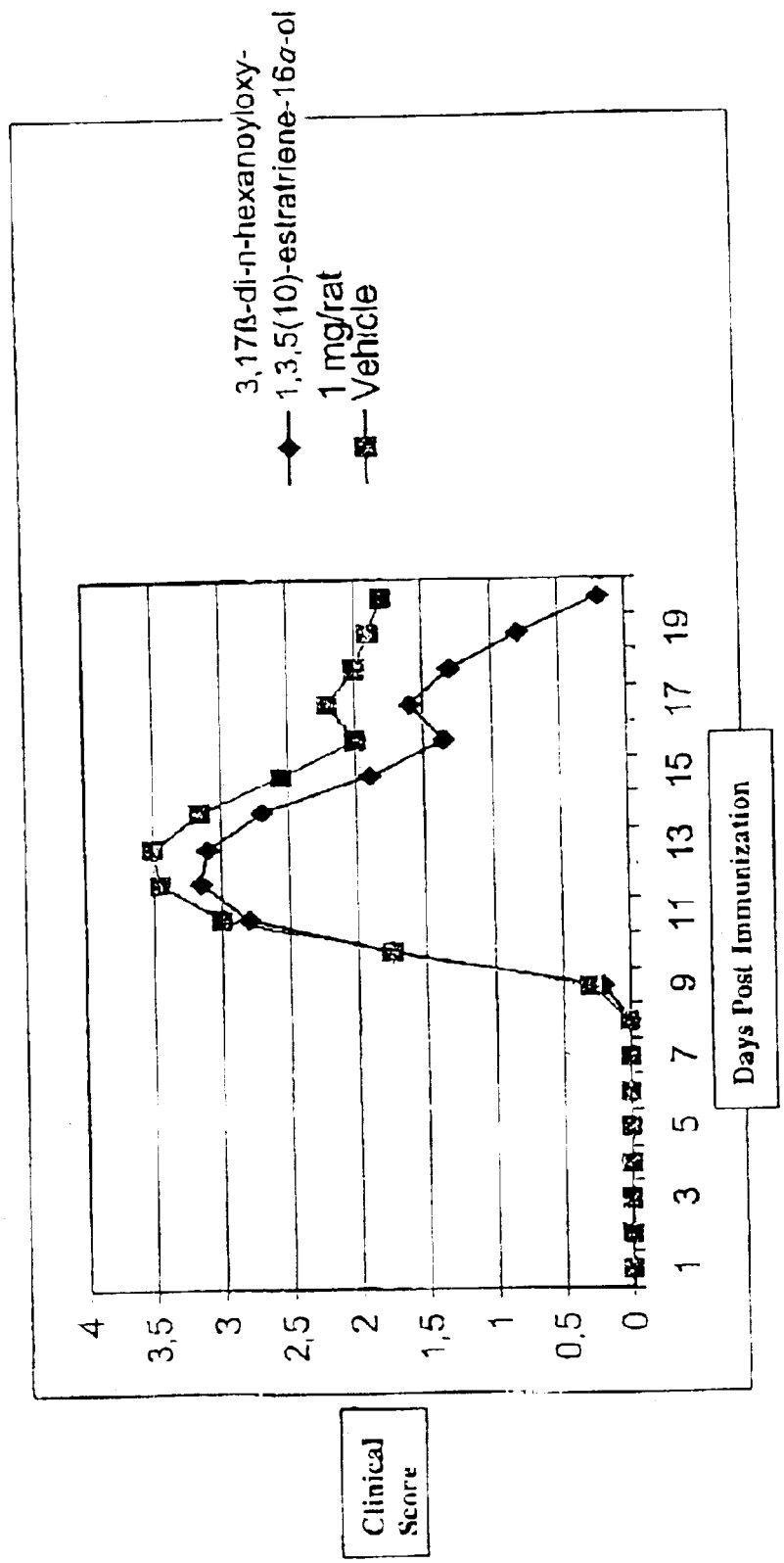
Fig. 1/1

USE OF BIOGENIC ESTRIOL DIESTER PRODRUGS FOR THE TREATMENT OF AUTOIMMUNE DISEASES

This application claims the benefit of the filing date of U.S. Provisional Application Ser. No. 60/359,726 filed Feb. 27, 2002.

FIELD OF THE INVENTION

The present invention relates to the use or esters of estriol, for example, an estriol 3,17-dipropionate or an estriol 3,17-dihexanoate, for the treatment of autoimmune diseases, such as multiple sclerosis (MS).

BACKGROUND OF THE INVENTION

Autoimmune diseases are a type of immune pathologies that result from an uncontrolled immune response against autoantigens. The susceptibility to autoimmune diseases is affected by gender. During reproductive ages, there exists a prevalence among females to suffer from an autoimmune disease such as multiple sclerosis (MS) or rheumatoid arthritis (RA). For example, the female-to-male ratio to develop MS is 2:1 (Voskuhl et al., 2001; Neuroscientist 7: 258–270; Whitacre et al., 1999; Science 283: 1277–1278).

MS is an autoimmune disorder of the central nervous system affecting the myelin sheath of neurons and leading to demyelination and subsequent neuronal cell death. The disease is mediated by CD4+ T lymphocytes, which are specific for proteins in the myelin sheath like myelin basic protein (MBP), proteolipid protein (PLP), and myelin oligodendrocyte protein. One hypothesis is that on the basis of a genetically determined predisposition, environmental factors such as viral infections trigger the outbreak of the disease which results in an imbalance in the Th1 and Th2 population of lymphocytes, thereby promoting the accumulation of activated Th1 cells that are able to penetrate the blood-brain barrier and exert proinflammatory actions in the CNS. Demyelination of axons is in part caused by myelin-specific CD4+ lymphocytes secreting Th1 cytokines like interleukin(IL)-12, interferon gamma (IFNγ) and tumour necrosis factor alpha (TNFα). This pro-inflammatory cytokine pattern is characteristic for the cell-mediated immune response. In healthy individuals the cell-mediated Th1 immune response is in balance with the humoral Th2 immune response.

The humoral immune response is mediated by the anti-inflammatory Th2 cytokines IL-4, IL-5 and IL-10.

The treatment strategies of MS are currently based on immunomodulatory treatment using interferons or glatiramer acetate. However, these treatments delay progress of disease only in some patients. Corticosteroids are used for acute treatment of relapses due to their antiinflammatory effects. Treatment with corticosteroids alleviates some acute symptoms of MS but fails to affect long-term prognosis. In addition to the known, numerous side-effects of corticosteroids, they also inhibit endogenous immunosuppressive mechanisms, rendering them unsuitable for long-term therapy. For therapy of highly active disease or of patients not responding to standard treatments including patients suffering from secondary progressive MS, immunosuppressive agents like methotrexate or cyclosporine are used. These substances are often poorly tolerated.

Therefore, there exists a need for an additional treatment strategy of MS and other Th1-mediated immune diseases.

In many autoimmune diseases, such as in MS, the Th1/Th2 balance is disturbed. Female sex hormones seem to have an influence on the regulation of this balance. During pregnancy, a shift toward a Th2 cytokine pattern has been demonstrated. An improvement of the clinical symptoms of Th1-mediated immune diseases (like MS) during pregnancy has also been observed. Especially in the third trimester of pregnancy, the rate of relapse declines in women with MS (Confavreux et al., 1998; N Engl J Med 339(5): 285–291). The decrease in disease activity appears to be due at least in part to high levels of estrogens such as estradiol and estriol, which are observed during the last trimester of pregnancy. In an animal model of MS, the Th1-mediated experimental autoimmune encephalomyelitis (EAE), it has been shown that administration of estriol at levels equal to those found in pregnancy were capable of ameliorating disease (Kim et al., 1999; Neurology 52: 1230–1238; Jansson et al., 1994, J Neuroimmunol 53: 203–207). Furthermore, it has been shown by Correale et al. (1998: J Immunol 161: 3365–3374) that the secretion of the anti-inflammatory cytokine IL-10 by CD4+ lymphocytes of MS patients is stimulated by estradiol, estrone and estriol at concentrations at a similar level as in pregnancy.

WO 01/85154 discloses a method of treating immune pathologies with low dose estrogen raising the serum concentration above basal level, but below pregnancy levels.

Because of the involvement of estrogens in the regulation of the balance between pro-inflammatory and anti-inflammatory conditions, a potential therapy for patients suffering from a Th1-mediated immune disease is to administer estrogens, in particular estriols, preferably to achieve continuous serum concentrations typically found in pregnancy.

However, the therapeutic use of estrogens is afflicted with several problems. One disadvantage of the use of estrogens in therapy is their potential ability to cause uterine cancer (endometrium carcinoma) or breast cancer. For example, the use of estradiol could lead to the metabolite 16alpha-hydroxyestrone, a metabolite with known tumor-promoting activity (Bradlow et al., 1985; Proc Natl Sci USA 82: 6295–6299; Kabat et al., 1997; Cancer Epidemiol Biomarkers Prev 6: 505–509).

Estriol as an active principle circumvents this problem. It is believed that estriol therapy is associated with small risks of cancer development in the human. Because of the much faster dissociation of estriol-estrogen receptor (ER) complexes than the dissociation of estradiol-ER complexes, estriol acts as a weaker and only short lasting estrogen. Therefore, estriol causes minimal endometrial proliferation. In addition, estriol displays antagonistic activity on the binding of estradiol to the receptor (Clark et al, 1984; J Steroid Biochem 20: 1005–1013) and therefore estriol seems to have a protective role opposing carcinogenic effects of estradiol. The antagonistic effects of estriol are only observed if the ratio of estriol to estradiol and estrone is 10:1, below this ratio estradiol is only partially or minimally antagonized and acts as a potent estrogen (Melamed et al, 1997; Mol Endocrinol 11: 1868–1878). This ratio is achieved in late pregnancy.

One problem encountered in the prior art is the inability to achieve continuous pregnancy blood levels of estriol with a form of administration that is comfortable for the patient. When administered orally, the bioavailability of estriol is low. To achieve comparable serum levels of estriol as after intravaginal application, ten times more estriol had to be administered orally (Head et al., 1998. Altern Med Rev 3: 101–113). Thus, estriol had to be orally administered in high doses, giving rise to possible side effects. Oral application of estriol leads to high estrogenicity in the liver. Hepatic effects include, for example, the increased synthesis of factors of the blood clotting system and angiotensinogen.

Another problem known from the prior art for oral therapy with estriol is that blood levels of estriol vary widely from patient to patient, so that general recommendations of the doses are not possible.

Problematic is also the very short half-life of estriol of about 1.5–5.3 h (Heithecker et al., 1991; Horm Res 35: 234–238). Thus, to achieve well-defined and sustained blood levels of estriol similar to those found in pregnancy, high doses of oral estriol would have to be administered at short time intervals which is not convenient for the patient, and several side effects have to be taken into account.

Increase of the orally administered dose of estriol is not the way to increase the desired systemic estrogenicity. Osteoprotective properties of estriol are a quite good marker for the systemic estrogenicity of estriol. EP 0 630 248 teaches that if estriol is administered transdermally in a system which continuously releases estriol for at least 24 h and thereby a constant blood level of estriol is achieved, estriol exhibits anti-osteoporotical effects. The decisive factor for these effects is the constant estriol blood level. Although Lindsay et al. (1979; Maturitas 1: 279–285) administered orally estriol in very high doses (12 mg/day), they were not able to show the osteoprotective effects.

EP 0 163 596 discloses estra-1,3,5(10)-triene ester derivatives, methods of preparing such compounds and pharmaceutical compositions containing them.

In view of the problems encountered by the prior art, a new therapeutic approach for the treatment of autoimmune diseases by achieving a well-defined and sustained blood level of estriol without the described disadvantages would be desirable.

OBJECTS OF THE PRESENT INVENTION

It is the object of the present invention to prevent or reduce the disadvantages of the prior art, i.e. to provide a new strategy for the treatment of autoimmune diseases, especially MS. In an aspect of the invention, the autoimmune disease is Th1-mediated.

The object is achieved by prodrugs of estriol, specifically estriol diesters, preferably, estriol 3,17-dipropionate or 3,17-dihexanoate. Most preferred is the estriol ester 3,17β-di-n-hexanoyloxy-1,3,5(10)-estratriene-16α-ol. The compound is a preferably parenterally administered prodrug and thereby liver-estriol interactions should be prevented. Estriol diester prodrugs such as 3,17β-di-n-hexanoyloxy-1,3,5(10)-estratriene-16α-ol achieve a well-defined and sustained blood level of estriol. Administration of the estriol diester prodrugs according to the invention, such as 3,17β-di-n-hexanoyloxy-1,3,5(10)-estratriene-16α-ol, causes a shift toward an anti-inflammatory Th2-type of immune response, and therefore, provides a promising method and use for ameliorating autoimmune diseases like MS.

SUMMARY OF THE INVENTION

The present invention relates to the use of estriol diester prodrugs for the preparation of a medicament for the treatment of an autoimmune disease such as MS in a mammal. Preferably, such estriol diester is an estriol 3,17-dipropionate or an estriol 3,17-dihexanoate. The most preferred estriol diester is 3,17β-di-n-hexanoyloxy-1,3,5(10)-estratriene-16α-ol. In particular, the administration of low doses of the invention estriol esters, such as 3,17β-di-n-hexanoyloxy-1,3,5(10)-estratriene-16α-ol, results in such high and sustained estriol blood levels as observed in late pregnancy, such as the second or third trimester of pregnancy, preferably during the last trimester, without any effects on hepatic functions.

In another aspect, the present invention provides a method for the treatment of autoimmune diseases such as MS in a mammal in need of such treatment, said method comprising administering a pharmaceutically effective amount of an estriol diester to a mammal in need thereof. For the invention methods and uses, 3,17β-di-n-hexanoyloxy-1,3,5(10)-estratriene-16α-ol is the most preferred estriol diester prodrug.

FIG. 1 represents the summary of the clinical scares (rat acute EAE model) for vehicle and 3,17β-di-n-hexanoyloxy-1,3,5(10)-estratriene-16α-ol-treated animals.

DETAILED DESCRIPTION OF THE INVENTION

The invention relates to the methods and uses of estriol diester prodrugs, such as 3,17β-di-n-hexanoyloxy-1,3,5(10)-estratriene-16α-ol, for the treatment of autoimmune diseases, such as MS.

Estriol diesters are represented by the general formula below:

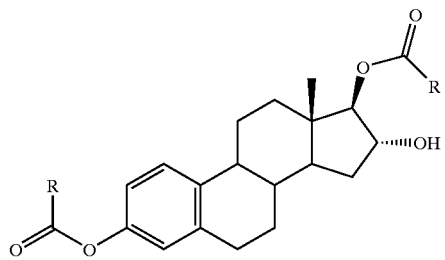

wherein R is a $C_{1\text{-}10}$ straight or branched alkyl group or phenyl.

The estriol diester for use in the invention is preferably an estriol 3,17-dipropionate or an estriol 3,17 dihexanoate. The most preferred compound for use in the invention is 3,17β-di-n-hexanoyloxy-1,3,5(10)-estratriene-16α-ol. Although 3,17β-di-n-hexanoyloxy-1,3,5(10)-estratriene-16α-ol is the preferred estriol diester for the purpose of the present invention, this does not exclude the possibility to use other suitable estriol diesters as well.

The term "prodrug" in the context of the present invention means a biologically inactive substance, which is metabolised to the active form in the organism.

Estriol diester prodrugs suitable for use in the invention and methods for their manufacture are described in EP 0 163 596. In particular, the method for preparing 3,17β-di-n-hexanoyloxy-1,3,5(10)-estratriene-16α-ol is described in Example 6 of EP 0 163 596.

The present invention provides a new therapy strategy for the treatment of autoimmune diseases, such as MS. It provides the possibility to achieve and to sustain blood levels of estriol as high as in the second or third trimester of pregnancy. This blood level is high enough to cause an immune shift in Th1-mediated immune diseases.

The superiority of the present invention over the prior art results from the high bioavailability of the estriol released from the diester prodrug compared to the conventionally used estriol (E3). The estriol diester prodrugs of the invention are particularly suitable for use in large dosage intervals. Due to the slow release of estriol from the diester prodrug, high, well-defined and sustained blood levels of estriol may be reached after administration of relatively low dosages. Preliminary studies by Heithecker et al. 1991 (Horm Res 35: 234–238) have shown that estriol diester derivatives increase estriol blood levels for much longer periods than estriol.

A favourable consequence of the administration of estriol esters as a prodrug for the purpose of the present invention is that much reduced interactions with liver functions during the first-pass can be observed. This has the advantage that the released estriol is well tolerated.

In a preferred aspect, the present invention relates to the use of estriol esters (e.g., estriol 3,17-propionate or estriol 3,17-dihexanoate) for the manufacture of a medicament for the treatment of an autoimmune disease. Preferably, the disease is a Th1-mediated autoimmune disease, most preferably, MS. The most preferred estriol diester prodrug is 3,17β-di-n-hexanoyloxy-1,3,5(10)-estratriene-15α-ol. Preferably, the medicament is for the treatment in a human.

In a second preferred aspect, the present invention relates to a method for the treatment of an autoimmune disease. Preferably, the disease is a Th1-mediated autoimmune disease, most preferably, MS. The method comprises administering estriol diester to a mammal, preferably a human, in need of such treatment. The estriol diester is preferably an estriol 3,17-dipropionate or an estriol 3,17-dihexanoate, most preferably the diester 3,17β-di-n-hexanoyloxy-1,3,5 (10)-estratriene-16α-ol.

Autoimmune diseases are caused in part by T cells, which recognize a host component (autoantigen) in a specific tissue (organspecific) or in various tissues as foreign and attack that tissue. Autoimmune diseases in the context of the present invention include, but are not limited to e.g. multiple sclerosis (MS), experimental autoimmune encephalomyelitis (EAE), rheumatoid arthritis, juvenile oligoarthritis, collagen-induced arthritis, type I diabetes mellitus, inflammatory bowel disease, Hashimoto's thyroiditis, Crohn's disease, Graft-versus-host-disease, lupus disorders, Addison's disease, and the like.

It is desirable that the prodrugs of the invention are administered in an amount sufficient to raise the serum concentration of estriol equivalent to pregnancy levels. For example, it has been observed that estriol is secreted in the order of 40 mg/24 h and circulates at a concentration of 1–100 ng/ml during late pregnancy in the blood (see, Katagiri et al, 1976, Am J Obstet Gynecol 272–280; Klopper et al, 1977, Obstet Gynecol, 459–461; Fischer-Rasmussen et al, 1981, Acta Obstet Gynecol Scand 417–420).

According to the invention, a diester prodrug of estriol of the general formula (see page 6) permits the uptake and/or binding of estriol in a metabolically stabilized form. Accordingly a high systemic estriol level may be achieved without hepatic estrogenicity side effects. Furthermore, because of the generated depot of estriol, a well-defined and sustained estriol blood level is obtained. The half-life of estriol in the organism is extended. Accordingly, the administration in large intervals is possible. Due to improved bioavailability, this can be achieved with relatively low dosages.

The advantages of the invention estriol diester prodrugs, such as the most preferred 3,17β-di-n-hexanoyloxy-1,3,5 (10)-estratriene-16α-ol, are numerous, namely:

1. reduction of side effects in the liver;
2. extension of the half-life of estriol in the organism; and
3. enhancement of the bioavailability.

As a consequence, the prodrugs according to the invention may be administered at relatively low dosages with, longer intervals between the doses. Furthermore, the individual variability among patients is decreased.

Due to the depot effect of the diesters, the frequency of the application for the purposes of the invention could be reduced in comparison to the application of estriol. The duration of the depot effect depends on the chain length of the esterificated mono carbonic acid.

The active agent suitable for the purposes of the present invention as defined above, e.g., estriol diesters such as 3,17β-di-n-hexanoyloxy-1,3,5(10)-estratriene-16α-ol, may be incorporated into pharmaceutical compositions according to known methods of preparing galenics.

The manufacture of the medicaments and pharmaceutical compositions for use in the invention may be performed according to methods known in the art. Commonly known and used adjuvants as well as further suitable carriers or diluents may be used. Suitable carriers and adjuvants may be such as recommended for pharmacy, cosmetics and related fields in: *Ullmann's Encyclopedia of Technical Chemistry*, Vol. 4, (1953), pp. 1–39; *Journal of Pharmaceutical Sciences*, Vol. 52 (1963), p. 918ff; H.v.Czetsch-Lindenwald, "Hilfsstoffe für Pharmazie und angrenzende Gebiete"; *Pharm. Ind.* 2, 1961, p.72ff; Dr. H. P. Fiedler, *Lexikon der Hilfsstoffe für Pharmazie, Kosmetik und angrenzende Gebiete*, Cantor K G, Aulendorf in Württemberg, 1971.

The administration of the estriol diester prodrugs of the invention, such as 3,17β-di-n-hexanoyloxy-1,3,5(10)-estratriene-16α-ol, as a medicament may be oral, rectal, intrauterine, intravaginal, local, transdermal or parenteral. The oral application could be in the form of powder, granules, tablets, pills, pastilles, dragees, capsules, fluid extracts, tinctures and syrups. Rectal or intravaginal application could be in the form of suppositories or intrauterine devices. Local application could be in the form of suspensions or emulsions, ointments, creams or gels. Transdermal could be in form of a patch. The parenteral application of injectable sterile aqueous or oily solutions or suspensions could be subcutaneous or intramuscular as well as percutaneous. The medicament according to the present invention may be administered via a depot injection or an implant preparation, optionally for sustained delivery of the active agent. The preferred mode of application is the administration via an injection.

Implants can comprise as inert materials e.g. biologically degradable polymers or synthetic silicones such as e.g. silicone rubber.

Suitable diluents for preparing a pharmaceutical composition are defined in EP 0 163 596.

The dose of the estriol diester prodrug of the invention such as 3,17β-di-n-hexanoyloxy-1,3,5(10)-estratriene-16α-ol, which has to be administered, can raise the serum concentration of estriol to 0.1–100 ng/ml. A serum concentration of estriol in the range of 0.1–100 ng/ml is desirable, more preferably in the range of 0.1–10 ng/ml, most preferably in the range of 1–10 ng/ml. According to the invention, this is achieved by the application of the estriol diester prodrugs of the invention in a cumulative dose of 1–1000 mg, preferably 10–500 mg per month. The interval between applications may be between 1 to 60 days, preferably 5–50, most preferably 20–40 days. Methods of measuring the estriol serum concentration are known in the art, for example, a suitable radioimmunassay is disclosed in Heithecker et al 1991 (Horm Res 35: 234–238).

Optionally, the pharmaceutical uses and methods according to the present invention further comprise other pharmaceutically active agents. For example, the pharmaceutically active agent may be a hormone, e.g., progesterone (gestagen), or a progesterone precursor, analog, progesterone receptor agonist or mesoprogestin. The combination of the compounds of the invention with, e.g., progesterone (gestagen) may have an additional protective effect against endometrial proliferation and certain other risks, associated with the long term use of estriol. A combination with testosterone or other androgens may be needed to avoid the loss of libido due to a loss of testosterone secretion.

The continuous administration of 3,17β-di-n-hexanoyloxy-1,3,5(10)-estratriene-16α-ol can lead to proliferation of the endometrium. This undesired effect in conjunction with estrogen treatment is withdrawn by the accompanying treatment with a progestin, e.g. "Kontrazeption mit Hormonen", H.-D. Taubert und H. Kuhl, Georg Thieme Verlag, Stuttgart, New York, 1995, or mesoprogestin (=progesterone antagonist with significant partial agonistic activity), e.g. compounds mentioned in EP 0648778 B1, EP 0648779 B1, EP 1157996 A1, WO 01/34126 and WO 99/45023. The progestin or the mesoprogestin can be administered in usual forms of administration and dosages and the administration may be e.g. oral, parenteral or intrauterine.

This treatment does not influence the course of the disease of multiple sclerosis. This accompanying treatment can be omitted in hysterectomized women.

The treatment of autoimmune diseases, for example Th1-mediated diseases, such as MS, with the invention estriol diester prodrug may further comprise the administration of a conventional immunotherapeutic agent. The term "immunotherapeutic agent" in the context of the present invention includes, but is not limited to, immunomodulatory or immunosuppressive agents such as corticosteroids, cyclosporine, FK 506, methotrexate, azathioprine, Mitoxantrone, cyclophosphamid, glatiramer acetate copolymer-1, anti-inflammatory cytokines such as IL-4, IL-5, IL-10, IFNβ, e.g. betaferon®, cytokine-antagonists such as against IL-1, IL-2 and IL-12, TNFα, antiinflammatory PDE IV receptor antagonists e.g. mesopram, integrin α 4 antagonists and antiinflammatory chemokine antagonists such as CCR1 receptor antagonists, including antibodies, antisense oligonucleotides and soluble receptors.

The estriol diester prodrug according to the invention such as 3,17β-di-n-hexanoyloxy-1,3,5(10)-estratriene-16α-ol, and the pharmaceutically active immunotherapeutic agent may be administered either together or separately, at the same time and/or sequentially. The mode of administration may differ between the prodrugs of the invention and the second pharmaceutically active agent.

Efficacy of 3,17β-di-n-hexanoyloxy-1,3,5(10)-estratriene-16α-ol in rat acute EAE Experimental Design:

In order to investigate the efficacy of 3,17β-di-n-hexanoyloxy-1,3,5(10)-estratriene-16α-ol in animal model of MS, this compound has been tested in the Lewis rat EAE model.

1. Disease Introduction

Female Lewis rats were immunized at 8 weeks of age with antigen emulsion. On day 1, rats were immunized with a 0.05 ml subcutaneous injection into each hind footpad with the following mixture: whole guinea pig spinal cord, homogenized and mixed 1 g:1 ml saline. This homogenate is then mixed 1:1 with Freund's incomplete adjuvant containing 1 mg/ml *Mycobacterium* tuberculosis. 0.05 ml of spinal cord homogenate (SCH) was injected by single bolus injections on day 1 into each hind limb footpad for a total of 0.1 ml per rat.

2. Treatment 3,17β-di-n-hexanoyloxy-1,3,5(10)-estratriene-16α-ol was prepared in a vehicle benzyl benzoate:castor oil (3:2 g/g). 3,17β-di-n-hexanoyloxy-1,3,5(10)-estratriene-16α-ol was dosed sub-cutaneously (s.c.) at 1000 ug/rat in 0.5 ml/injection. 3,17β-di-n-hexanoyloxy-1,3,5(10)-estratriene-16α-ol was administered twice during this study (on day 1 and day 15). Solution was prepared fresh before each dose 3,17β-di-n-hexanoyloxy-1,3,5(10)-estratriene-16α-ol first dissolved in benzyl benzoate and gently heated before addition of castor oil. There were 10 animals per each group (vehicle-benzyl benzoate/castor oil and treated—1000 ug/rat 3,17β-di-n-hexanoyloxy-1,3,5(10)-estratriene-16α-ol).

3. Clinical Evaluation

Clinical evaluation was performed according to the well established protocol. EAE score of zero means that animal had no neurological symptoms and was classified as normal. Clinical score of 1 means that animal had a limp tail and 2 represents incomplete paralysis of one or both hind limbs. Animals with the complete paralysis of one hind limb or both hind limbs can move but do not help in movement of the body are scored as 3. EAE score of 4 represents complete paralysis of both hind limbs and 5 is complete paralysis of hind limbs and weakness of one or both forelimbs or moribund, or death.

Rats were weighed and scored every few days up to day 4, then weighed and scored daily up to day 20. Plasma and serum samples were collected for blood chemistry analysis.

Rats which are borderline in scores are given a one half score, such as 3.5.

Results and Conclusions:

3,17β-di-n-hexanoyloxy-1,3,5(10)-estratriene-16α-ol was efficacious in lowering the clinical score in Lewis rat EAE model during the chronic stage of a disease. The clinical scores for the vehicle and 3,17β-di-n-hexanoyloxy-1,3,5(10)-estratriene-16α-ol treated animals are represented in FIG. 1. Analyzing the scores conducting an ANOVA there is a significant difference between the vehicle and 3,17β-di-n-hexanoyloxy-1,3,5(10)-estratriene-16α-ol treated animals in the chronic stage of the disease ($p \leq 0.028$).

These results suggest that 3,17β-di-n-hexanoyloxy-1,3,5(10)-estratriene-16α-ol might be a potential therapeutic for the treatment of autoimmune demyelination that could be administrated twice a month or less and still exhibit its protective effect.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding European Patent Application No. 02090160.9, filed Apr. 30, 2002, and U.S. Provisional Application Ser. No. 60/359,726, filed Feb. 27, 2002 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method of treating an autoimmune disease in a mammal comprising administering a pharmaceutically effective amount of an estriol ester having the general formula,

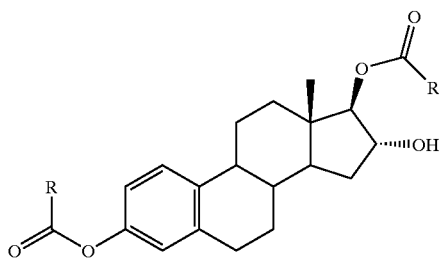

wherein R is a $C_{1-10}$ straight or branched alkyl group or phenyl, to a mammal in need thereof.

2. The method of claim 1, wherein the estriol ester is estriol 3,17-dipropionate or estriol 3,17-dihexanoate.

3. The method of claim 1, wherein the estriol ester is 3,17β-di-n-hexanoyloxy-1,3,5(10)-estratriene-16α-ol.

4. The method of claim 1, wherein the mammal is a human.

5. The method of claim 1, wherein the autoimmune disease involves a Th1-mediated immune response.

6. The method of claim 1, wherein the disease is selected from the group consisting of multiple sclerosis, rheumatoid arthritis, juvenile oligoarthritis, type I diabetes mellitus, inflammatory bowel disease, Hashimoto's thyroiditis, Addison's disease, lupus disorders, acute graft-versus-host disease, and Crohn's disease.

7. The method of claim 1, wherein the disease is multiple sclerosis.

8. The method of claim 1, wherein the estriol ester is administered in a cumulative dose of 1–1000 mg per month.

9. The method of claim 1, wherein treatment further comprises the administration of a second therapeutic agent.

10. The method of claim 1, wherein the pharmaceutically effective amount of the estriol ester is to be administered subcutaneously or intramuscularly by injection.

11. Method for providing a blood level of estriol as observed during late pregnancy comprising administering an effective amount of an estriol ester having the general formula,

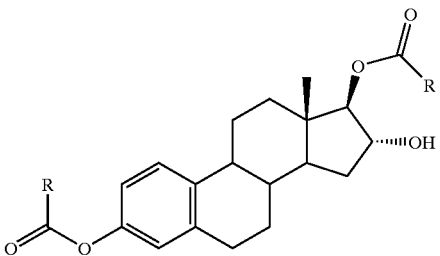

wherein R is a $C_{1-10}$ straight or branched alkyl group or phenyl, to a mammal in need thereof.

12. The method of claim 11, wherein the estriol ester is estriol 3,17-dipropionate or estriol 3,17-dihexanoate.

13. The method of claim 11, wherein the estriol ester is 3,17β-di-n-hexanoyloxy-1,3,5(10)-estratriene-16α-ol.

14. The method of claim 11, wherein the estriol blood level is between 0.1–100 ng/ml.

15. The method of claim 11, wherein the pharmaceutically effective amount of the estriol ester is to be administered subcutaneously or intramuscularly by injection.

* * * * *